US006783770B2

United States Patent
Angel et al.

(10) Patent No.: US 6,783,770 B2
(45) Date of Patent: Aug. 31, 2004

(54) HARD CAPSULES COMPRISING POLYMERS OF VINYL ESTERS AND POLYETHERS, THEIR USE AND PRODUCTION

(75) Inventors: Maximilian Angel, Schifferstadt (DE); Karl Kolter, Limburgerhof (DE); Axel Sanner, Frankenthal (DE); Michael Gotsche, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/811,542

(22) Filed: Mar. 20, 2001

(65) Prior Publication Data

US 2001/0036471 A1 Nov. 1, 2001

(30) Foreign Application Priority Data

Mar. 29, 2000 (DE) ........................................ 100 15 468

(51) Int. Cl.⁷ ................................................ A61K 9/48
(52) U.S. Cl. ........................................................ 424/451
(58) Field of Search ................................. 424/451, 440

(56) References Cited

U.S. PATENT DOCUMENTS

| 3,984,494 A | * 10/1976 | Harreus et al. ............. 264/301 |
| 5,972,508 A | * 10/1999 | Boeckh et al. ............. 427/213.3 |
| 6,579,953 B1 | * 6/2003 | Gotsche et al. ............. 525/451 |

FOREIGN PATENT DOCUMENTS

| DE | 1 077 430 | 3/1960 |
| DE | 1 081 229 | 5/1960 |
| DE | 1 094 457 | 12/1960 |
| DE | 1 965 584 | 7/1970 |
| DE | 23 63 853 | 7/1975 |
| EP | 408 311 A2 | 1/1991 |
| EP | 408 311 | 1/1991 |
| EP | 743 962 | 11/1996 |
| EP | 743 962 B1 | 11/1996 |
| EP | 1 136 070 | 9/2001 |
| GB | 922 457 | 4/1963 |
| GB | 922 458 | 4/1963 |
| GB | 1 298 084 | 11/1972 |
| JP | 45-1277 | 7/1970 |
| WO | WO 9827151 A1 * | 6/1998 ............. C08L/1/26 |
| WO | WO 00/18375 | 4/2000 |

OTHER PUBLICATIONS

Abstract JA 76–04794—JA–7001 277.

* cited by examiner

Primary Examiner—Thurman K. Page
Assistant Examiner—Robert M. Joynes
(74) Attorney, Agent, or Firm—Keil & Weinkauf

(57) ABSTRACT

The present invention relates to hard capsules comprising (A) polymers obtainable by free-radical polymerization of a) at least one vinyl ester in the presence of
    b) polyether-containing compounds and
    c) where appropriate one or more other copolymerizable monomers c) and subsequent at least partial hydrolysis of the ester functions in the original monomers a), with the proviso that in the absence of another copolymerizable monomer c) the polyether-containing compound b) must have a number average molecular weight $\leq 10,000$, (B) where appropriate structure-improving auxiliaries and
(C) other conventional shell constituents, the production and use thereof.

18 Claims, No Drawings

HARD CAPSULES COMPRISING POLYMERS OF VINYL ESTERS AND POLYETHERS, THEIR USE AND PRODUCTION

The present invention relates to hard capsules, for example for pharmaceutical applications, comprising polymers prepared by polymerization of vinyl esters and, where appropriate, another free-radically copolymerizable monomer in the presence of a polyether-containing compound, and subsequent at least partial hydrolysis, comprising structure-improving auxiliaries and other conventional shell constituents, their use and production.

Hard capsules are distinguished by being produced as empty capsules which are in two pieces which fit together, and being filled and closed only after production. The hard capsules are in most cases produced from aqueous solution in the so-called dip process (S. Stegmann, PZ Prisma, 5, 42–56, 1998). A review of the prior art in injection molding for producing pharmaceutical hard capsules from starch or gelatin is given by L. Eith et al. in Drug Dev. Ind. Pharm., 12, 2113–2126 (1986). On detailed examination of this processing, it is clear that the two parts of the capsule must be very mechanically stable, especially since the filling machines are very fast-running and dimensional changes would have very adverse effects on the filling process.

Since the two molded parts are tightly fitted together after filling, it is necessary that the capsule material has adequate dimensional stability.

In addition, hard capsules for medical applications are frequently packed in so-called blister packs to increase the storage stability. When the hard capsules are pushed out of these packs, mechanical stress occurs and must not lead to deformation of the hard capsules. It is therefore necessary for hard capsules to have adequate mechanical stability.

To date, hard capsules for pharmaceutical dosage forms have been mainly produced from gelatin. However, gelatin has some crucial disadvantages. Thus, gelatin is a material of animal origin and is thus not kosher. In addition, there is always a slight residual risk of BSE because gelatin from cattle is preferably used to produce them. Obtaining a suitable gelatin is very complicated and requires strict monitoring of the process. Nevertheless, differences between batches are large because of the animal origin, which is subject to a certain variability. Gelatin is very microbially susceptible because it represents a good nutrient medium for microorganisms. Appropriate measures must therefore be taken during production and use of such packaging materials. The use of preservatives is frequently indispensable.

Since gelatin is per se a brittle material of low flexibility, it must be plasticized appropriately, i.e. plasticizers must be added in the form of low molecular weight compounds. These plasticizers which are necessary frequently migrate from the shell into the filling and cause changes there. The shell loses plasticizers and becomes brittle and mechanically unstable during the course of storage.

The rate of dissolution of gelatin is relatively slow. A higher rate of dissolution in gastric or intestinal fluid would be desirable for rapid release of active ingredients.

Numerous substances lead to interactions with gelatin, such as, for example, aldehydes, polyphenols, reducing sugars, multiply charged cations, electrolytes, cationic or anionic polymers etc., with crosslinking frequently occurring and the capsule then disintegrating or dissolving only very slowly or not at all. Such changes are catastrophic for a drug product because efficacy is lost. Many drugs also lead to interactions with gelatin. In some cases during storage there is formation of drug degradation products with, for example, an aldehyde structure, which lead to crosslinking of the gelatin. Since gelatin has both acidic and basic groups, it is clear that reactions easily occur with other charged molecules.

Gelatin can be cleaved by enzymes. Contamination by enzymes or bacteria which release enzymes may drastically alter the properties of gelatin.

Because of these many disadvantages, there has been no lack of attempts to replace gelatin wholly or partly in hard capsules.

Attempts have therefore been made to find synthetic polymers which can be employed to produce hard capsules.

For example, polyvinyl alcohol has been described for this purpose. However, polyvinyl alcohol has a slow rate of dissolution, likewise requires additional plasticizers, which in turn may migrate and which, as already described above, may alter the properties of the filling, and it may moreover become extremely brittle as a consequence of internal crystallization.

In particular, the flexibility decreases drastically during the course of storage if the ambient humidity is low.

JP Sho-45-1277 used, for example, polyvinyl alcohol as base material for hard capsules. DE-A-1 965 584 likewise describes the use of polyvinyl alcohol and other polymers for medicinal hard capsules.

These polymers have not proved to be an adequate substitute for conventional gelatin in the technology and practice of capsule production and use thereof.

DE-A 23 63 853 describes self-supporting packings or capsules for medicines which are produced using graft copolymers of polyvinyl alcohol on polyethylene glycol. The graft copolymers preferred for this application are produced by grafting vinyl acetate onto polyethylene glycol having a molecular weight of from 20,000 to 25,000 and subsequent methanolysis of the vinyl acetate units. Such polymers are very soft and easily deformable.

Graft copolymers of polyvinyl alcohol on polyalkylene glycols have already been described in other patents.

DE 1 077 430 describes a process for producing graft copolymers of vinyl esters on polyalkylene glycols.

DE 1 094 457 and DE 1 081 229 describe processes for producing graft copolymers of polyvinyl alcohol on polyalkylene glycols by hydrolyzing the vinyl esters and the use thereof as protective colloids, water-soluble packaging films, as sizing and finishing agents for textiles and in cosmetics.

The use of the described graft copolymers for hard capsules has not been disclosed.

The polymers described in the prior art to date have inadequate properties for the production of hard capsules because of their elasticity and flexibility.

It is an object of the present invention to find synthetic polymers with greater dimensional stability for producing hard capsules for pharmaceutical dosage forms which are superior to gelatin and many known substitute materials.

We have found that this object is achieved by hard capsules comprising (A) polymers obtainable by free-radical polymerization of
   a) at least one vinyl ester in the presence of
   b) polyether-containing compounds and
   c) where appropriate one or more other copolymerizable monomers and subsequent at least partial hydrolysis of the ester functions in the original monomers a),
with the proviso that in the absence of another copolymerizable monomer c) the polyether-containing compound b) must have a number average molecular weight $\leq 10{,}000$, (B) where appropriate structure-improving auxiliaries and
(C) other conventional shell constituents.

It has moreover been found, surprisingly, that addition of another comonomer c) in the polymerization in particular leads to harder polymers which are suitable for producing hard capsules with improved dimensional stability.

During production of the polymers used according to the invention there may be during the polymerization a grafting onto the polyether-containing compounds (b), which may lead to the advantageous properties of the polymers. However, mechanisms other than grafting are also conceivable.

Depending on the degree of grafting, the polymers used according to the invention comprise both pure graft copolymers and mixtures of the abovementioned graft copolymers with ungrafted polyether-containing compounds and homo- or copolymers of monomers a) and c).

Polyether-containing compounds (b) which can be used are both polyalkylene oxides based on ethylene oxide, propylene oxide, butylene oxide and other alkylene oxides, and polyglycerol. Depending on the nature of the monomer building blocks, the polymers contain the following structural units.

—$(CH_2)_2$—O—, —$(CH_2)_3$—O—, —$(CH_2)_4$—O—, —$CH_2$—$CH(R^6)$—O—, —$CH_2$—$CHOR^7$—$CH_2$—O— with $R^6$ $C_1$–$C_{24}$-alkyl;
$R^7$ hydrogen, $C_1$–$C_{24}$-alkyl, $R^6$—C(=O)—, $R^6$—NH—C(=O)—.

It is moreover possible for the structural units to be both homopolymers and random copolymers and block copolymers.

The polyethers (b) preferably used are polymers of the general formula I

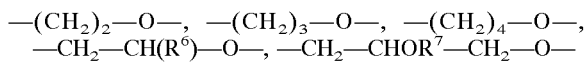

in which the variables have, independently of one another, the following meaning:

$R^1$ hydrogen, $C_1$–$C_{24}$-alkyl, $R^6$—C(=O)—, $R^6$—NH—C(=O)—, polyalcohol residue;
$R^5$ hydrogen, $C_1$–$C_{24}$-alkyl, $R^6$—C(=O)—, $R^6$—NH—C(=O)—;
$R^2$ to $R^4$ —$(CH_2)_2$—, —$(CH_2)_3$—, —$(CH_2)_4$—, —$CH_2$—$CH(R^6)$—, —$CH_2$—$CHOR^7$—$CH_2$—;
$R^6$ $C_1$–$C_{24}$-alkyl;
$R^7$ hydrogen, $C_1$–$C_{24}$-alkyl, $R^6$—C (=O)—, $R^6$—NH—C(=O)—;
A —C(=O)—O, —C(=O)—B—C(=O)—O, —C(=O)—NH—B—NH—C(=O)—O;
B —$(CH_2)_t$—, arylene, optionally substituted;
n 1 to 1000;
s 0 to 1000;
t 1 to 12;
u 1 to 5000;
v 0 to 5000;
w 0 to 5000;
x 0 to 5000;
y 0 to 5000;
z 0 to 5000, with the proviso that in the absence of another copolymerizable monomer c), n is 1 to 200;
s is 0 to 200;
t is 1 to 12;
u is 1 to 250;
v is 0 to 250;
w is 0 to 250;
x is 0 to 250;
y is 0 to 250;
z is 0 to 250, and the molecular weight of the polyether is ≦10,000.

The terminal primary hydroxyl groups of the polyethers prepared based on polyalkylene oxides, and the secondary OH groups of polyglycerol, may be in unprotected form, may be etherified or esterified with $C_1$–$C_{24}$ alcohols or carboxylic acids, respectively, or may be reacted with isocyanates to give urethanes.

Alkyl radicals which may be mentioned for $R^1$ and $R^5$ to $R^7$ are branched or unbranched $C_1$–$C_{24}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 2-ethylhexyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Preferred representatives of the abovementioned alkyl radicals which may be mentioned are branched or unbranched $C_1$–$C_{12}$-, particularly preferably $C_1$–$C_6$-alkyl chains.

The number average molecular weight of the polyethers is in the range below 1,000,000, preferably in the range from 300 to 100,000, particularly preferably in the range from 500 to 50,000, very particularly preferably in the range from 800 to 40,000. In the absence of another copolymerizable monomer c) the number average molecular weight of the polyethers is in the range below and up to 10,000, preferably in the range from 300 to 10,000, particularly preferably in the range from 500 to 10,000.

It is advantageous to use homopolymers of ethylene oxide or copolymers with an ethylene oxide content of from 40 to 99% by weight. Thus, the content of ethylene oxide units in the ethylene oxide polymers to be preferably employed is from 40 to 100 mol %. Suitable comonomers for these copolymers are propylene oxide, butylene oxide and/or isobutylene oxide. Suitable examples are copolymers of ethylene oxide and propylene oxide, copolymers of ethylene oxide and butylene oxide, and copolymers of ethylene oxide, propylene oxide and at least one butylene oxide. The ethylene oxide content of the copolymers is preferably from 40 to 99 mol %, the propylene oxide content is from 1 to 60 mol % and the content of butylene oxide in the copolymers is from 1 to 30 mol %. Not only straight-chain but also branched homo- or copolymers can be used as polyether-containing compounds b).

Branched polymers can be produced by, for example, adding ethylene oxide and, where appropriate, also propylene oxide and/or butylene oxides onto polyalcohol residues, for example onto pentaerythritol, glycerol or onto sugar alcohols such as D-sorbitol and D-mannitol, as well as onto polysaccharides such as cellulose and starch. The alkylene oxide units in the polymer may be randomly distributed or present in the form of blocks.

However, it is also possible to use polyesters of polyalkylene oxides and aliphatic or aromatic dicarboxylic acids, for example oxalic acid, succinic acid, adipic acid and terephthalic acid, with molecular weights of from 1500 to 25,000 as described, for example, in EP-A-0 743 962, as polyether-containing compound. A further possibility is also to use polycarbonates through reaction of polyalkylene oxides with phosgene or carbonates such as, for example, diphenyl carbonate, and polyurethanes through reaction of polyalkylene oxides with aliphatic and aromatic diisocyanates.

The numbers in parentheses hereinafter relate to the case where no additional copolymerizable monomer c) is present.

Particularly preferred polyethers (b) are polymers of the general formula I with a number average molecular weight of from 300 to 100,000 (10,000), in which the variables have, independently of one another, the following meaning:

$R^1$ hydrogen, $C_1$–$C_{12}$-alkyl, $R^6$—C(=O)—, $R^6$—NH—C(=O)—, polyalcohol residue;
$R^5$ hydrogen, $C_1$–$C_{12}$-alkyl, $R^6$—C(=O)—, $R^6$—NH—C(=O)—;
$R^2$ to $R^4$ —(CH$_2$)$_2$—, —(CH$_2$)$_3$—, —(CH$_2$)$_4$—, —CH$_2$—CH($R^6$)—, —CH$_2$—CHOR$^7$—CH$_2$—;
$R^6$ $C_1$–$C_{12}$-alkyl;
$R^7$ hydrogen, $C_1$–$C_{12}$-alkyl, $R^6$—C(=O)—, $R^6$—NH—C(=O)—;
n 1 to 8 (1 to 8);
s 0 (0);
u 2 to 2000 (250);
v 0 to 2000 (250);
w 0 to 2000 (250).

Very particularly preferred polyethers b) are polymers of the general formula I with a number average molecular weight of from 500 to 50,000 (10,000), in which the variables have, independently of one another, the following meaning:

$R^1$ hydrogen, $C_1$–$C_6$-alkyl, $R^6$—C(=O)—, $R^6$—NH—C(=O)—;
$R^5$ hydrogen, $C_1$–$C_6$-alkyl, $R^6$—C(=O)—, $R^6$—NH—C(=O)—;
$R^2$ to $R^4$ —(CH$_2$)$_2$—, —(CH$_2$)$_3$—, —(CH$_2$)$_4$—, —CH$_2$—CH($R^6$)—, —CH$_2$—CHOR$^7$—CH$_2$—;
$R^6$ $C_1$–$C_6$-alkyl;
$R^7$ hydrogen, $C_1$–$C_6$-alkyl, $R^6$—C(=O)—, $R^6$—NH—C(=O)—;
n 1 (1);
s 0 (0);
u 5 to 500 (250);
v 0 to 500 (250);
w 0 to 500 (250).

Further polyethers (b) which can be used are homo- and copolymers of polyalkylene oxide-containing ethylenically unsaturated monomers such as, for example, polyalkylene oxide (meth)acrylates, polyalkylene oxide vinyl ethers, polyalkylene oxide-(meth)acrylamides, polyalkylene oxide-allylamides or polyalkylene oxide-vinylamides. It is, of course, also possible to employ copolymers of such monomers with other ethylenically unsaturated monomers.

The following monomers capable of free-radical polymerization may be mentioned as component a) for the polymerization in the presence of the polyethers b):

Vinyl esters of aliphatic, saturated or unsaturated $C_1$–$C_{24}$-carboxylic acids such as, for example, formic acid, acetic acid, propionic acid, butyric acid, valeric acid, isovaleric acid, caproic acid, caprylic acid, capric acid, undecylenic acid, lauric acid, myristic acid, palmitic acid, palmitoleic acid, stearic acid, oleic acid, arachidic acid, behenic acid, lignoceric acid, cerotic acid and melissic acid.

It is preferred to use vinyl esters of the abovementioned $C_1$–$C_{12}$-carboxylic acids, in particular of the $C_1$–$C_6$-carboxylic acids. Vinyl acetate is very particularly preferred.

It is, of course, also possible to copolymerize mixtures of the particular monomers from group a).

To adjust to the required mechanical properties it is possible to employ in addition to the vinyl ester (a) at least one ethylenically unsaturated copolymerizable comonomer (c). The proportion of these additional monomers is preferably between 0 and 50% by weight, very particularly preferably between 0 and 20% by weight. The term ethylenically unsaturated means that the monomers have at least one carbon-carbon double bond which is capable of free-radical polymerization and which may be mono-, di-, tri- or tetrasubstituted.

The preferred employed ethylenically unsaturated comonomers (c) can be described by the following general formula:

X—C(O)CR$^{15}$=CHR$^{14}$ where

X is selected from the group of radicals —OH, —OM, —OR$^{16}$, NH$_2$, —NHR$^{16}$, N(R$^{16}$)$_2$;
M is a cation selected from the group consisting of: Na$^+$, K$^+$, Mg$^{++}$, Ca$^{++}$, Zn$^{++}$, NH$_4^+$, alkylammonium, dialkylammonium, trialkylammonium and tetraalkylammonium;
the R$^{16}$ radicals can be identical or different and selected from the group consisting of —H, linear- or branched-chain $C_1$–$C_{40}$-alkyl radicals, N,N-dimethylaminoethyl, 2-hydroxyethyl, 2-methoxyethyl, 2-ethoxyethyl, hydroxypropyl, methoxypropyl or ethoxypropyl.
R$^{15}$ and R$^{14}$ are, independently of one another, selected from the group consisting of: —H, linear- or branched-chain $C_1$–$C_8$-alkyl chains, methoxy, ethoxy, 2-hydroxyethoxy, 2-methoxyethoxy and 2-ethoxyethyl.

Representative but non-limiting examples of suitable monomers (c) are, for example, acrylic acid or methacrylic acid and their salts, esters and amides. The salts may be derived from any nontoxic metal, ammonium or substituted ammonium counterions.

The esters may be derived from linear $C_1$–$C_{40}$, branched-chain $C_3$–$C_{40}$ or carbocyclic $C_3$–$C_{40}$ alcohols, from polyfunctional alcohols with 2 to about 8 hydroxyl groups, such as ethylene glycol, hexylene glycol, glycerol and 1,2,6-hexanetriol, from amino alcohols or from alcohol ethers such as methoxyethanol and ethoxyethanol, (alkyl)polyethylene glycols, (alkyl)polypropylene glycols or ethoxylated fatty alcohols, for example $C_{12}$–$C_{24}$-fatty alcohols reacted with 1 to 200 ethylene oxide units.

Also suitable are N,N-dialkylaminoalkyl acrylates and methacrylates and N,N-dialkylaminoalkylacrylamides and -methacrylamides of the general formula (III)

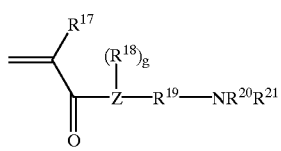

(III)

with $R^{17}$=H, alkyl with 1 to 8 C atoms,
$R^{18}$=H, methyl,
$R^{19}$=alkylene with 1 to 24 C atoms, optionally substituted by alkyl,
$R^{20}$, $R^{21}$=$C_1$–$C_{40}$-alkyl radical,
Z=nitrogen for g=1 or oxygen for g=0.

The amides may be unsubstituted, N-alkyl- or N-alkylamino-monosubstituted or N,N-dialkyl-substituted or N,N-dialkylamino-disubstituted, in which the alkyl or alkylamino groups are derived from linear $C_1$–$C_{40}$, branched-chain $C_3$–$C_{40}$ or carbocyclic $C_3$–$C_{40}$ units. The alkylamino groups may additionally be quaternized.

Preferred comonomers of formula III are N,N-dimethylaminomethyl (meth)acrylate, N,N-diethylaminomethyl (meth)acrylate, N,N-dimethylaminoethyl (meth)acrylate, N,N-diethylaminoethyl (meth)acrylate, N-[3-(dimethylamino)propyl] methacrylamide and N-[3-(dimethylamino)propyl] acrylamide.

Comonomers (c) which can likewise be used are substituted acrylic acids and salts, esters and amides thereof, where the substituents are located on the carbon atoms in position two or three of the acrylic acid, and are selected, independently of one another, from the group consisting of $C_1$–$C_4$-alkyl, —CN, COOH, particularly preferably methacrylic acid, ethacrylic acid and 3-cyanoacrylic acid. These salts, esters and amides of these substituted acrylic acids may be selected as described above for the salts, esters and amides of acrylic acid.

Other suitable comonomers (c) are allyl esters of linear $C_1$–$C_{40}$, branched-chain $C_3$–$C_{40}$ or carbocyclic $C_3$–$C_{40}$ carboxylic acids, vinyl or allyl halides, preferably vinyl chloride and allyl chloride, vinyl ethers, preferably methyl, ethyl, butyl or dodecyl vinyl ether, vinylformamide, vinylmethylacetamide, vinylamine; vinyllactams, preferably vinylpyrrolidone and vinylcaprolactam, vinyl- or allyl-substituted heterocyclic compounds, preferably vinylpyridine, vinyloxazoline and allylpyridine.

Also suitable are N-vinylimidazoles of the general formula IV in which $R^{22}$ to $R^{24}$ are, independently of one another, hydrogen, $C_1$–$C_4$-alkyl or phenyl:

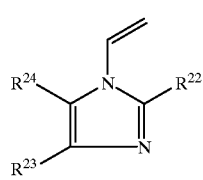

(IV)

Further suitable comonomers (c) are diallylamines of the general formula (V)

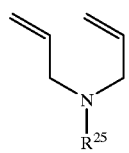

(V)

with $R^{25}$=$C_1$- to $C_{24}$-alkyl.

Further suitable comonomers (c) are vinylidene chloride; and hydrocarbons having at least one carbon-carbon double bond, preferably styrene, alpha-methylstyrene, tert-butylstyrene, butadiene, isoprene, cyclohexadiene, ethylene, propylene, 1-butene, 2-butene, isobutylene, vinyltoluene, and mixtures of these monomers.

Particularly suitable comonomers (c) are acrylic acid, methacrylic acid, ethacrylic acid, methyl acrylate, ethyl acrylate, propyl acrylate, n-butyl acrylate, isobutyl acrylate, t-butyl acrylate, 2-ethylhexyl acrylate, decyl acrylate, methyl methacrylate, ethyl methacrylate, propyl methacrylate, n-butyl methacrylate, isobutyl methacrylate, t-butyl methacrylate, 2-ethylhexyl methacrylate, decyl methacrylate, methyl ethacrylate, ethyl ethacrylate, n-butyl ethacrylate, isobutyl ethacrylate, t-butyl ethacrylate, 2-ethylhexyl ethacrylate, decyl ethacrylate, stearyl (meth) acrylate, 2,3-dihydroxypropyl acrylate, 2,3-dihydroxypropyl methacrylate, 2-hydroxyethyl acrylate, hydroxypropyl acrylates, 2-hydroxyethyl methacrylate, 2-hydroxyethyl ethacrylate, 2-methoxyethyl acrylate, 2-methoxyethyl methacrylate, 2-methoxyethyl ethacrylate, 2-ethoxyethyl methacrylate, 2-ethoxyethyl ethacrylate, hydroxypropyl methacrylates, glyceryl monoacrylate, glyceryl monomethacrylate, polyalkylene glycol (meth) acrylates, unsaturated sulfonic acids such as, for example, acrylamidopropanesulfonic acid;

acrylamide, methacrylamide, ethacrylamide, N-methylacrylamide, N,N-dimethylacrylamide, N-ethylacrylamide, N-isopropylacrylamide, N-butylacrylamide, N-t-butylacrylamide, N-octylacrylamide, N-t-octylacrylamide, N-octadecylacrylamide, N-phenylacrylamide, N-methylmethacrylamide, N-ethylmethacrylamide, N-dodecylmethacrylamide, 1-vinylimidazole, 1-vinyl-2-methylvinylimidazole, N,N-dimethylaminomethyl (meth) acrylate, N,N-diethylaminomethyl (meth)acrylate, N,N-dimethylaminoethyl (meth)acrylate, N,N-diethylaminoethyl (meth)acrylate, N,N-dimethylaminobutyl (meth)acrylate, N,N-diethylaminobutyl (meth)acrylate, N,N-dimethylaminohexyl (meth)acrylate, N,N-dimethylaminooctyl (meth)acrylate, N,N-dimethylaminododecyl (meth)acrylate, N-[3-(dimethylamino)propyl]methacrylamide, N-[3-(dimethylamino)propyl]acrylamide, N-[3-(dimethylamino)butyl]methacrylamide, N-[8-(dimethylamino)octyl]methacrylamide, N-[12-(dimethylamino)dodecyl]methacrylamide, N-[3-(diethylamino)propyl]methacrylamide, N-[3-(diethylamino)propyl]acrylamide;

maleic acid, fumaric acid, maleic anhydride and its monoesters, crotonic acid, itaconic acid, diallyldimethylammonium chloride, vinyl ethers (for example: methyl, ethyl, butyl or dodecyl vinyl ether), vinylformamide, vinylmethylacetamide, vinylamine; methyl vinyl ketone, maleimide, vinylpyridine, vinylimidazole, vinylfuran, styrene, styrenesulfonate, allyl alcohol, and mixtures thereof.

Of these, particular preference is given to acrylic acid, methacrylic acid, maleic acid, fumaric acid, crotonic acid, maleic anhydride and its monoesters, methyl acrylate, methyl methacrylate, ethyl acrylate, ethyl methacrylate, n-butyl acrylate, n-butyl methacrylate, t-butyl acrylate, t-butyl methacrylate, isobutyl acrylate, isobutyl methacrylate, 2-ethylhexyl acrylate, stearyl acrylate, stearyl methacrylate, N-t-butylacrylamide, N-octylacrylamide, 2-hydroxyethyl acrylate, hydroxypropyl acrylates, 2-hydroxyethyl methacrylate, hydroxypropyl methacrylates, alkylene glycol (meth)acrylates, styrene, unsaturated sulfonic acids such as, for example, acrylamidopropanesulfonic acid, vinylpyrrolidone, vinylcaprolactam, vinyl ethers (for example: methyl, ethyl, butyl or dodecyl vinyl ether), vinylformamide, vinylmethylacetamide, vinylamine, 1-vinylimidazole, 1-vinyl-2-methylimidazole, N,N-dimethylaminomethyl methacrylate and N-[3-(dimethylamino)propyl]methacrylamide; 3-methyl-1-vinylimidazolium chloride, 3-methyl-1-vinylimidazolium methyl sulfate, N,N-dimethylaminoethyl methacrylate, N-[3-(dimethylamino)propyl]methacrylamide quaternized with methyl chloride, methyl sulfate or diethyl sulfate.

Monomers with a basic nitrogen atom may moreover be quaternized in the following way:

Suitable for quaternizing the amines are, for example, alkyl halides with 1 to 24 C atoms in the alkyl group, for example methyl chloride, methyl bromide, methyl iodide, ethyl chloride, ethyl bromide, propyl chloride, hexyl chloride, dodecyl chloride, lauryl chloride and benzyl halides, in particular benzyl chloride and benzyl bromide. Further suitable quaternizing agents are dialkyl sulfates, in particular dimethyl sulfate or diethyl sulfate. The quaternization of the basic amines can also be carried out with alkylene oxides such as ethylene oxide or propylene oxide in the presence of acids. Preferred quaternizing agents are: methyl chloride, dimethyl sulfate or diethyl sulfate.

The quaternization can be carried out before the polymerization or after the polymerization.

It is additionally possible to employ the products of the reaction of unsaturated acids, such as, for example, acrylic acid or methacrylic acid, with a quaternized epichlorohydrin of the general formula (VI) ($R^{26}=C_1$- to $C_{40}$-alkyl).

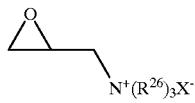

(VI)

Examples thereof are:
(meth)acryloyloxyhydroxypropyltrimethylammonium chloride and (meth)acryloyloxyhydroxypropyltriethylammonium chloride.

The basic monomers can also be cationized by neutralizing them with mineral acids such as, for example, sulfuric acid, hydrochloric acid, hydrobromic acid, hydroiodic acid, phosphoric acid or nitric acid, or with organic acids such as, for example, formic acid, acetic acid, lactic acid or citric acid.

In addition to the abovementioned comonomers, it is possible to employ as comonomers (c) so-called macromonomers such as, for example, silicone-containing macromonomers with one or more groups capable of free-radical polymerization, or alkyloxazoline macromonomers as described, for example, in EP 408 311.

It is further possible to employ fluorine-containing monomers as described, for example, in EP 558423, and compounds which have a crosslinking action or regulate the molecular weight, in combination or alone.

Regulators which can be used are the usual compounds known to the skilled worker, such as, for example, sulfur compounds (e.g.: mercaptoethanol, 2-ethylhexyl thioglycolate, thioglycolic acid or dodecyl mercaptan), and tribromochloromethane or other compounds which have a regulating effect on the molecular weight of the resulting polymers.

It is also possible where appropriate to employ thiol-containing silicone compounds.

Silicone-free regulators are preferably employed.

The advantageous mechanical properties can also be achieved by using crosslinking monomers as monomers c). The term crosslinking means that the monomers have at least two ethylenic double bonds, such as, for example, esters of ethylenically unsaturated carboxylic acids such as acrylic acid or methacrylic acid and polyhydric alcohols, ethers of at least dihydric alcohols, such as, for example, vinyl ethers or allyl ethers.

Examples of the underlying alcohols are dihydric alcohols such as 1,2-ethanediol, 1,2-propanediol, 1,3-propanediol, 1,2-butanediol, 1,3-butanediol, 2,3-butanediol, 1,4-butanediol, 2-butene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis(hydroxymethyl)cyclohexane, hydroxypivalic acid neopentyl glycol monoester, 2,2-bis(4-hydroxyphenyl) propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiapentane-1,5-diol, and polyethylene glycols, polypropylene glycols and polytetrahydrofurans with molecular weights of, in each case, from 200 to 10,000. Apart from the homopolymers of ethylene oxide or propylene oxide, it is also possible to employ block copolymers of ethylene oxide or propylene oxide or copolymers containing incorporated ethylene oxide and propylene oxide groups. Examples of underlying alcohols with more than two OH groups are trimethylolpropane, glycerol, pentaerythritol, 1,2,5-pentanetriol, 1,2,6-hexanetriol, triethoxycyanuric acid, sorbitan, sugars such as sucrose, glucose, mannose. It is, of course, also possible for the polyhydric alcohols to be employed after reaction with ethylene oxide or propylene oxide as the corresponding ethoxylates or propoxylates. The polyhydric alcohols can also be firstly converted into the corresponding glycidyl ethers by reaction with epichlorohydrin.

Further suitable crosslinkers are the vinyl esters or the esters of monohydric unsaturated alcohols with ethylenically unsaturated $C_3$- to $C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. However, the monohydric unsaturated alcohols can also be esterified with polybasic carboxylic acids, for example malonic acid, tartaric acid, trimellitic acid, phthalic acid, terephthalic acid, citric acid or succinic acid. Further suitable crosslinkers are esters of unsaturated carboxylic acids with the polyhydric alcohols described above, for example of oleic acid, crotonic acid, cinnamic acid or 10-undecenoic acid.

Also suitable are straight-chain or branched, linear or cyclic aliphatic or aromatic hydrocarbons which have at least two double bonds which, in the case of the aliphatic hydrocarbons, must not be conjugated, for example divinylbenzene, divinyltoluene, 1,7-octadiene, 1,9-decadiene, 4-vinyl-1-cyclohexene, trivinylcyclohexane or polybutadienes with molecular weights of from 200 to 20,000.

Also suitable are amides of unsaturated carboxylic acids such as, for example, acrylic and methacrylic acids, itaconic acid, maleic acid, and N-allylamines of at least difunctional amines, such as, for example, diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Likewise suitable are the amides from allylamine and unsaturated carboxylic acids such as acrylic acid, methacrylic acid, itaconic acid, maleic acid, or at least dibasic carboxylic acids like those described above.

Further suitable crosslinkers are triallylamine or corresponding ammonium salts, for example triallylmethylammonium chloride or methyl sulfate.

It is further possible to employ N-vinyl compounds of urea derivatives, at least difunctional amides, cyanurates or urethanes, for example of urea, ethyleneurea, propyleneurea or tartaramide, for example N,N'-divinylethyleneurea or N,N'-divinylpropyleneurea.

Further suitable crosslinkers are divinyldioxane, tetraallylsilane and tetravinylsilane.

Examples of particularly preferred crosslinkers are methylenebisacrylamide, divinylbenzene, triallylamine and triallylammonium salts, divinylimidazole, N,N'-divinylethyleneurea, products of the reaction of polyhydric alcohols with acrylic acid or methacrylic acid, methacrylic esters and acrylic esters of polyalkylene oxides or polyhydric alcohols which have been reacted with ethylene oxide and/or propylene oxide and/or epichlorohydrin, and allyl or vinyl ethers of polyhydric alcohols, for example 1,2-ethanediol, 1,4-butanediol, diethylene glycol, trimethylolpropane, glycerol, pentaerythritol, sorbitan and sugars such as sucrose, glucose, mannose.

Very particularly preferred crosslinkers are pentaerythritol triallyl ether, allyl ethers of sugars such as sucrose, glucose, mannose, divinylbenzene, methylenebisacrylamide, N,N'-divinylethyleneurea, and (meth)acrylic esters of glycol, butanediol, trimethylolpropane or glycerol or (meth)acrylic esters of glycol, butanediol, trimethylolpropane or glycerol reacted with ethylene oxide and/or epichlorohydrin.

The proportion of the monomers with a crosslinking action is from 0 to 10% by weight, preferably 0 to 5% by weight, very particularly preferably 0 to 2% by weight.

The comonomers (c) according to the invention can, if they contain ionizable groups, be partly or completely neutralized with acids or bases before or after the polymerization, in order, for example, in this way to adjust the solubility or dispersibility in water to a desired extent.

Neutralizing agents which can be used for monomers with acidic groups are, for example, mineral bases such as sodium carbonate, alkali metal hydroxides, and ammonia, organic bases such as amino alcohols, specifically 2-amino-2-methyl-1-propanol, monoethanolamine, diethanolamine, triethanolamine, triisopropanolamine, tri(2-hydroxy-1-propyl)amine, 2-amino-2-methyl-1,3-propanediol, 2-amino-2-hydroxymethyl-1,3-propanediol, and diamines such as, for example, lysine.

To prepare the polymers, the monomers of component a) can be polymerized in the presence of the polyethers both with the aid of free radical-forming initiators and by exposure to high-energy radiation, which is intended to include the exposure to high-energy electrons.

The initiators which can be employed for the free-radical polymerization are the peroxo and/or azo compounds customary for this purpose, for example alkali metal or ammonium peroxodisulfates, diacetyl peroxide, dibenzoyl peroxide, succinyl peroxide, di-tert-butyl peroxide, tert-butyl perbenzoate, tert-butyl perpivalate, tert-butyl peroxy-2-ethylhexanoate, tert-butyl permaleate, cumene hydroperoxide, diisopropyl peroxydicarbonate, bis(o-toluyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, azobisisobutyronitrile, azobis(2-amidinopropane) dihydrochloride or 2,2'-azobis(2-methylbutyronitrile). Also suitable are initiator mixtures or redox initiator systems such as, for example, ascorbic acid/iron(II) sulfate/sodium peroxodisulfate, tert-butyl hydroperoxide/sodium disulfite, tert-butyl hydroperoxide/sodium hydroxymethanesulfinate.

Organic peroxides are preferably employed.

The amounts of initiator or initiator mixtures used based on monomer employed are between 0.01 and 10% by weight, preferably between 0.1 and 5% by weight.

The polymerization takes place at a temperature in the range from 40 to 200° C., preferably in the range from 50 to 140° C., particularly preferably in the range from 60 to 110° C. It is normally carried out under atmospheric pressure, but can also take place under reduced or elevated pressure, preferably between 1 and 5 bar.

The polymerization can be carried out, for example, as solution polymerization, bulk polymerization, emulsion polymerization, inverse emulsion polymerization, suspension polymerization, inverse suspension polymerization or precipitation polymerization without the methods which can be used being restricted thereto.

The procedure for bulk polymerization can be such that the polyether-containing compound b) is dissolved in at least one monomer of group a) and, where appropriate, one or more comonomers of group c) and, after addition of a polymerization initiator, the mixture is completely polymerized. The polymerization can also be carried out semicontinuously by initially introducing part, for example 10% of the mixture to be polymerized of the polyether-containing compound b), at least one monomer of group a), where appropriate one or more comonomers of group c) and initiator, heating the mixture to polymerization temperature and, after the polymerization has started, adding the remainder of the mixture to be polymerized in accordance with the progress of the polymerization. The polymers can also be obtained by introducing the polyether-containing compounds of group b) into a reactor and heating to the polymerization temperature, and adding at least one monomer of group a), where appropriate one or more comonomers of group c) and polymerization initiator, either all at once, batchwise or, preferably, continuously, and polymerizing.

If required, the polymerization described above can also be carried out in a solvent. Examples of suitable solvents are alcohols such as methanol, ethanol, n-propanol, isopropanol, n-butanol, sec-butanol, tert-butanol, n-hexanol and cyclohexanol, and glycols such as ethylene glycol, propylene glycol and butylene glycol, and the methyl or ethyl ethers of the dihydric alcohols, diethylene glycol, triethylene glycol, glycerol and dioxane. The polymerization can also be carried out in water as solvent. In this case, a solution is initially present, which is more or less soluble in water depending on the amount of the added monomers of component a). In order to dissolve water-insoluble products which may be produced during the polymerization it is possible, for example, to add organic solvents such as monohydric alcohols with 1 to 3 carbon atoms, acetone or dimethylformamide. However, the procedure for the polymerization in water can also be such that the water-insoluble polymers are converted into a fine-particle dispersion by adding conventional emulsifiers or protective colloids, for example polyvinyl alcohol.

Examples of emulsifiers used are ionic or nonionic surfactants whose HLB is in the range from 3 to 13. For the definition of the HLB, reference is made to the publication by W. C. Griffin, J. Soc. Cosmetic Chem., volume 5, 249 (1954).

The amount of surfactants is from 0.1 to 10% by weight, based on the polymer. Use of water as solvent results in solutions or dispersions of the polymers. If solutions of the polymer are prepared in an organic solvent or in mixtures of an organic solvent and water, then from 5 to 2000, preferably 10 to 500, parts by weight of the organic solvent or mixture of solvents are used per 100 parts by weight of the polymer.

Preferred polymers are obtainable by free-radical polymerization of a) 10 to 98% by weight of at least one vinyl ester of $C_1$–$C_{24}$-carboxylic acids in the presence of
b) 2 to 90% by weight of at least one polyether-containing compound and
c) 0 to 50% by weight of one or more other copolymerizable monomers.

Particularly preferred polymers are obtainable by free-radical polymerization of a) 50 to 97% by weight of at least one vinyl ester of $C_1$–$C_{24}$-carboxylic acids in the presence of
b) 3 to 50% by weight of at least one polyether-containing compound and
c) 0 to 20% by weight of one or more other copolymerizable monomers.

Very particularly preferred polymers are obtainable by free-radical polymerization of a) 65 to 97% by weight of at least one vinyl ester of $C_1$–$C_{24}$-carboxylic acids in the presence of
b) 3 to 35% by weight of at least one polyether-containing compound and
c) 0 to 20% by weight of one or more other copolymerizable monomers.

To prepare the polymers used according to the invention, the ester groups in the original monomers a) and, where appropriate, other monomers are cleaved after the polymerization by hydrolysis, alcoholysis or aminolysis. This process step is generally referred to as hydrolysis hereinafter. The hydrolysis takes place in a manner known per se by adding a base, preferably by adding a sodium or potassium hydroxide solution in water and/or alcohol. Methanolic sodium or potassium hydroxide solutions are particularly preferably employed. The hydrolysis is carried out at temperatures in the range from 10 to 80° C., preferably in the range from 20 to 60° C. The degree of hydrolysis depends on the amount of base employed, on the hydrolysis temperature, the hydrolysis time and the water content of the solution.

The degree of hydrolysis of the polyvinyl ester groups is in the range from 1 to 100%, preferably in the range from 40 to 100%, particularly preferably in the range from 65 to 100%, very particularly preferably in the range from 80 to 100%.

The polymers prepared in this way can be subsequently cationized by reacting hydroxyl and/or amino functions present in the polymer with epoxides of the formula VI ($R^{26}$=$C_1$- to $C_{40}$- alkyl).

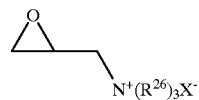

(VI)

It is possible and preferred for the hydroxyl groups of the polyvinyl alcohol units and vinylamine units produced by hydrolysis of vinylformamide to be reacted with the epoxides.

The epoxides of the formula VI can also be generated in situ by reacting the corresponding chlorohydrins with bases, for example sodium hydroxide.

2,3-Epoxypropyltrimethylammonium chloride or 3-chloro-2-hydroxypropyltrimethylammonium chloride is preferably employed.

The K values of the polymers should be in the range from 10 to 300, preferably 25 to 250, particularly preferably 25 to 200, very particularly preferably in the range from 30 to 150. The K value required in each case can be adjusted in a manner known per se by the composition of the starting materials. The K values are determined by the method of Fikentscher, Cellulosechemie, Vol. 13, pp. 58 to 64 and 71 to 74 (1932) in N-methylpyrrolidone at 25° C. and polymer concentrations which are between 0.1% by weight and 5% by weight, depending on the K value range.

After the hydrolysis, the polymer solutions can be steam distilled to remove solvents. The steam distillation results in aqueous solutions or dispersions, depending on the degree of hydrolysis and nature of the polyethers b), of the vinyl esters a) and of the possibly employed monomers c).

The mechanical properties of the polymers for producing hard capsules for pharmaceutical dosage forms can, however, also be beneficially influenced by subsequent crosslinking.

The invention also therefore relates to the use of polymers obtainable by free-radical polymerization of a) at least one vinyl ester of $C_1$–$C_{24}$-carboxylic acids in the presence of
b) polyether-containing compounds
c) where appropriate one or more copolymerizable monomers and subsequent at least partial hydrolysis of the ester functions in the original monomers a), for producing hard capsules, wherein the resulting polymers are subsequently crosslinked by a polymer-analogous reaction.

The subsequent crosslinking in this can take place by reacting the hydroxyl groups or amino groups in the polymer with at least bifunctional reagents. Water-soluble products are obtained with low degrees of crosslinking, while water-swellable or insoluble products are obtained with high degrees of crosslinking.

The polymers according to the invention can be reacted, for example, with dialdehydes and diketones, for example glyoxal, glutaraldehyde, succinaldehyde or terephthalaldehyde. Also suitable are aliphatic or aromatic carboxylic acids, for example maleic acid, oxalic acid, malonic acid, succinic acid or citric acid, or carboxylic acid derivatives such as carboxylic esters or anhydrides or carbonyl halides. Polyfunctional epoxides are also suitable, for example epichlorohydrin, glycidyl methacrylate, ethylene glycol diglycidyl ether, 1,4-butanediol diglycidyl ether or 1,4-bis (glycidyloxy)benzene. Also suitable are diisocyanates, for example hexamethylene diisocyanate, isophorone diisocyanate, methylenediphenyl diisocyanate, tolylene diisocyanate or divinyl sulfone.

Additionally suitable are inorganic compounds such as boric acid or boric acid salts, for example sodium metaborate, borax (disodium tetraborate), and salts of multiply charged cations, for example copper(II) salts such as copper(II) acetate or zinc, aluminum or titanium salts.

Boric acid or boric acid salts such as sodium metaborate or disodium tetraborate are suitable and preferred for the subsequent crosslinking. This may entail adding the boric acid or boric acid salts, preferably as salt solutions, to the solutions of the polymers according to the invention. The boric acid or boric acid salts are preferably added to the aqueous polymer solutions.

The boric acid or boric acid salts can be added to the polymer solutions immediately after preparation. However, it is also possible for the boric acid or boric acid salts to be added subsequently to the cosmetic formulations with the polymers according to the invention or during the cosmetic formulation production process.

The proportion of boric acid or boric acid salts based on the polymers according to the invention is from 0 to 15% by weight, preferably 0 to 10% by weight, particularly preferably 0 to 5% by weight.

The solutions and dispersions of the polymers according to the invention can be converted into powder form by various drying processes such as, for example, spray drying, fluidized spray drying, drum drying or freeze drying. Spray drying is preferably employed as drying process. An aqueous solution or dispersion can be prepared again by dissolving or redispersing the dry polymer powder obtained in this way in water. The conversion into powder form has the advantage of better storability, simpler transportability and less tendency to microbial attack.

In place of the steam-distilled polymer solutions, it is also possible to convert the alcoholic polymer solutions directly into powder form.

The water-soluble or water-dispersible polymers according to the invention containing polyalkylene oxide or polyglycerol are outstandingly suitable for producing hard capsules for pharmaceutical dosage forms.

The polymers can be produced with high reproducibility in the abovementioned processes. No materials of animal origin are used to produce them and, since no vegetable materials are employed either, the problem of products of genetic engineering origin does not arise.

The polymers are not particularly microbiologically susceptible because they do not represent good nutrient media for microorganisms. The polymer chains are not degraded either by enzymes or by hydrolysis. The preparation of solutions to produce films and for encapsulation is therefore no problem either.

Typical packaged materials are preferably pharmaceutical products such as solid and liquid active ingredients, but also vitamins, carotenoids, minerals, trace elements, food supplements, spices and sweeteners. The capsules can also be used for cosmetic active ingredients (personal care), such as, for example, hair and skin formulations, for oils, perfumes, bath additives or proteins. Further applications in the personal care sector, and further applications for water-soluble packagings are mentioned in Wo 99/40156.

Further possible examples of such packaged materials are cleaners, such as soaps, detergents, colorants and bleaches, agrochemicals such as fertilizers (or combinations thereof), crop protection agents such as herbicides, fungicides or pesticides, and seeds.

Solid filling material is preferably packed in hard capsules.

It is possible in general to use the polymers according to the invention to package contents which are to be protected before they are brought into a wet environment.

The rate of dissolution of the polymers according to the invention and of hard capsules produced therefrom is extremely high and markedly exceeds that of gelatin and polyvinyl alcohol. In addition, the polymers are soluble in cold water. Gelatin and polyvinyl alcohol dissolve only at higher temperatures. Since many drugs are intended to act quickly after intake, this dissolving behavior is a clear advantage in particular for this use.

In contrast to gelatin, it is also possible to encapsulate in the shells according to the invention substances prone to interactions, such as, for example, aldehydes or multiply charged cations. No slowing of the rate of dissolution is evident.

Hard capsules of the composition according to the invention can be coated extremely well using aqueous polymer solutions or polymer suspensions. Thus, a coating which is resistant to gastric fluid and adheres strongly to the surface and, moreover, is stable on storage can be applied by spraying on Kollicoat MAE 30 DP (USP type C methacrylic acid copolymer) in a horizontal drum coater.

To achieve resistance to gastric fluid it is additionally possible for the shell to comprise from 20 to 80%, preferably 30 to 70%, of a polymer resistant to gastric fluid.

It is possible to add to the polymers structure-improving auxiliaries in order to modify the mechanical properties such as flexibility and strength. These structure-improving auxiliaries can be divided into 2 large groups:

A) polymers with a molecular weight greater than 50,000, preferably greater than 100,000
B) substances which lead to crosslinking of the polymer chains of the polymers, preferably aldehydes, boric acid and its salts, and, where appropriate, substances which lead to crosslinking of the polymer chains of the structure-improving auxiliaries, preferably alkaline earth metal ions, amines, tannins, and aldehydes and borates.

High molecular weight polymers which can be employed are substances from the following classes:

polyamino acids such as gelatin, zein, soybean protein and derivatives thereof,
polysaccharides such as starch, degraded starch, maltodextrins, carboxymethylstarch, cellulose, hydroxypropylmethylcellulose, hydroxypropylcellulose, hydroxyethylcellulose, methylcellulose, carboxymethylcellulose, ethylcellulose, cellulose acetate, cellulose acetate phthalate, hydroxypropylcellulose acetate phthalate, hydroxypropylcellulose acetate succinate, hemicellulose, galactomannans, pectins, alginates, carrageenans, xanthan, gellan, dextran, curdlan, pullulan, chitin, and derivatives thereof, synthetic polymers such as polyacrylic acid, polymethacrylic acid, copolymers of acrylic esters and methacrylic esters, polyvinyl alcohols, polyvinyl acetate, polyethylene glycols, polyoxyethylene/polyoxypropylene block copolymers, polyvinylpyrrolidones and derivatives thereof.

These high molecular weight polymers form a network with the polymers and thus increase the strength of the hard capsules. The flexibility is usually not compromised as long as the concentrations used are not very high. Surprisingly, not only water-soluble but also water-insoluble polymers such as copolymers of acrylic esters and methacrylic esters are suitable for this purpose. The capsules still disintegrate as long as the concentration of these water-insoluble polymers remains below 50%.

Substances which lead to crosslinking either of the polymer chains of the polymers or of the added high molecular weight polymers act in a similar way.

Besides the components mentioned, it is possible for the hard capsules according to the invention to comprise other conventional constituents. These include fillers, release agents, flow aids, stabilizers and water-soluble or water-insoluble dyes, flavorings and sweeteners.

Examples of dyes are iron oxides, titanium dioxide, which are added in an amount of about 0.001 to 10, preferably of 0.5 to 3, % by weight, triphenylmethane dyes, azo dyes, quinoline dyes, indigo dyes, carotenoids, in order to color the capsules, opacifiers such as titanium dioxide or talc in order to decrease the transparency and save on dyes.

Flavorings and sweeteners are particularly important when an unpleasant odor or taste is to be masked and the capsule is chewed.

Preservatives are usually unnecessary.

Examples of fillers are inorganic fillers such as oxides of magnesium, aluminum, silicon, titanium or calcium carbonate. The preferred concentration range for the fillers is about 1 to 50% by weight, particularly preferably 2 to 30% by weight, based on the total weight of all the components.

Lubricants are stearates of aluminum, calcium, magnesium and tin, and magnesium silicate, silicones and the like. The preferred concentration range is about 0.1 to 5% by weight, particularly preferably about 0.1 to 3% by weight, based on the total weight of all the components.

Examples of flow aids are fine-particle or extremely fine-particle silicas, modified where appropriate. The preferred concentration range is 0.05 to 3% by weight, particularly preferably 0.1 to 1% by weight, based on the total weight of all the components.

Suitable additives for improving the thermoplastic properties of the compositions are also thermoplastic polymers such as polyethylene, polypropylene, polyisobutylene, polystyrene, polyacrylonitrile, polyvinylcarbazoles, polyacrylate, polymethacrylate, polyvinyl chloride, polyvinyl acetate, polyamide, polyester, polyurethane, polycarbonate, polyalkylene terephthalate, and copolymers of ethylene/vinyl acetate, ethylene/vinyl alcohol, ethylene/(meth)acrylic acid, ethylene/(meth)acrylic esters, ABS copolymer, SAN copolymers, ethylene/maleic anhydride copolymers. The graft copolymer used as starting material according to the invention can be mixed with various known additives such as fillers, release agents, flow aids, plasticizers, stabilizers and/or coloring agents.

The incorporation of active ingredients into the shell represents a special case. This may be advantageous for separating incompatible active ingredients from one another. The active ingredient with the smallest dose should then be incorporated into the shell.

The shell of the packaging materials according to the invention consists of 10 to 100%, preferably 20 to 98%, polymers, where appropriate 0 to 80%, preferably 1.9 to 50%, structure-improving auxiliaries and 0.1 to 30% other conventional constituents.

The following examples are intended to illustrate the invention in more detail without, however, restricting it thereto.

PREPARATION METHOD FOR EXAMPLES 1 to 14 AND FOR COMPARATIVE EXAMPLES 15 to 18

The polyether-containing compound is introduced into a polymerization vessel and heated to 80° with stirring under a gentle stream of nitrogen. Vinyl acetate and, where appropriate, the other monomer are metered in with stirring over the course of 3 h. Simultaneously, a solution of 1.4 g of tert-butyl peroxy-2-ethylhexanoate in 30 g of methanol is added, likewise over the course of 3 h. The mixture is then stirred at 80° C. for 2 h. After cooling, the polymer is dissolved in 450 ml of methanol. For the hydrolysis, 50 ml of a 10% strength methanolic sodium hydroxide solution are added at 30° C. After about 40 min, the reaction is stopped by adding 750 ml of 1% strength acetic acid. The methanol is removed by distillation.

The K values were determined on 1% solutions in N-methylpyrrolidone.

Films are cast from the polymers produced in this way, and the elongation at break is determined at 54% relative humidity. The dimensional stability after storage for 4 weeks was tested on capsule parts produced individually by dipping. This revealed that the elongation at break correlates very well with the dimensional stability. It was not possible to produce dimensionally stable capsules from the polymers when the elongations at break were high.

TABLE

| Example | Grafting base (1) | Vinyl ester | Comonomer | K value | Degree of hydrolysis [%] | Elongation at break [%] | Dimensional stability of the produced capsules |
|---|---|---|---|---|---|---|---|
| 1 | PEG 6000, 72 g | vinyl acetate, 396 g | methyl methacrylate, 12 g | 47 | >95 | 21 | dimensionally stable |
| 2 | PEG 20000 72 g | vinyl acetate, 328 g | N-vinylpyrrolidone, 82 g | 61 | >95 | 20 | dimensionally stable |
| 3 | PEG 20000, 72 g | vinyl acetate, 362 g | 3-methyl-1-vinyl-imidazolium methyl sulfate, 48 g | 53 | >95 | 40 | dimensionally stable |

TABLE-continued

| Example | Grafting base (1) | Vinyl ester | Comonomer | K value | Degree of hydrolysis [%] | Elongation at break [%] | Dimensional stability of the produced capsules |
|---|---|---|---|---|---|---|---|
| 4 | PEG 6000, 72 g | vinyl acetate, 367 g | N-vinylformamide, 41 g | 57 | >95 | 35 | dimensionally stable |
| 5 | PEG 6000, 72 g | vinyl acetate, 326 g | N-vinylformamide, 82 g | 67 | >95 | 25 | dimensionally stable |
| 6 | PEG 35000, 270 g | vinyl acetate, 410 g | pentaerythritol triallyl ether, 1.6 g | 71 | 95 | 20 | dimensionally stable |
| 7 | PEG 35000, 270 g | vinyl acetate, 410 g | pentaerytliritol triallyl ether, 0.8 g | 65 | 94 | 40 | dimensionally stable |
| 8 | PEG 35000, 270 g | vinyl acetate, 410 g | N,N'-divinylethylene urea, 0.7 g | 73 | 95 | 42 | dimensionally stable |
| 9 | PEG 1500 72 g | vinyl acetate, 410 g | — | 47 | >95 | 17 | dimensionally stable |
| 10 | PEG 4000 72 g | vinyl acetate, 410 g | — | 51 | >95 | 32 | dimensionally stable |
| 11 | PEG 6000, 72 g | vinyl acetate, 410 g | — | 54 | >95 | 42 | dimensionally stable |
| 12 | PEG 6000, 137 g | vinyl acetate, 410 g | — | 49 | >95 | 46 | dimensionally stable |
| 13 | PEG 6000, 22 g | vinyl acetate, 410 g | — | 73 | >95 | 23 | dimensionally stable |
| 14 | PEG-PPG-Block-copolymer 8000[2], 72 g | vinyl acetate, 410 g | — | 45 | >95 | 65 | dimensionally stable |
| 15 | PEG 20000 273 g | vinyl acetate, 410 g | | 62 | 93 | 180 | not dimensionally stable |
| 16 | PEG 35000 273 g | vinyl acetate 410 | | 59 | 94 | 404 | not dimensionally stable |
| 17 | PEG 20000 72 g | vinyl acetate, 410 g | | 60 | 93 | 141 | not dimensionally stable |
| 18 | PEG 35000 72 g | vinyl acetate 410 | | 65 | 94 | 280 | not dimensionally stable f |

(1) PEG x: Polyethylene glycol with average molecular weight x

EXAMPLE 19

A 5% strength aqueous solution of disodium tetraborate (Borax) is added to a stirred 19.3% strength aqueous solution of the polymer from Example 16 at room temperature over the course of half an hour. An increase in viscosity is observed. Addition of the Borax solution results in the capsules produced from the polymers becoming dimensionally stable.

| Amount of added 5% borax solution [g] | Brookfield viscosity (LVF, spindle 2, 30 rpm, 23° C.) [mPas] | Dimensional stability of the produced capsules |
|---|---|---|
| 0 (corresponds to Comparative Example 16) | 110 | not dimensionally stable |
| 21.0 | 534 | dimensionally stable |
| 24.0 | 2228 | dimensionally stable |
| 26.9 | 7520[1] | dimensionally stable |
| 29.8 | 29190[2] | dimensionally stable |

[1]Spindle 4, 30 rpm
[2]Spindle 4, 6 rpm

EXAMPLE 20

Hard capsules of size 0 were produced by the dip process. The two halves of the capsules were produced separately.

400 g of polymer of vinyl acetate and polyethylene glycol 6000 in the ratio 95:5 were dissolved with stirring in 600 g of demineralized water at 70° C. Care must be taken during this that no foam is produced. Into this solution were dipped vertically stainless steel pins rounded at the end and made hydrophobic with a silicone emulsion, and were withdrawn and dried in a stream of warm air at 90° C. while being continuously rotated about their own axis. The continuous rotation is important because, otherwise, the wall thickness becomes non-uniform. The pins for the body had a diameter of 7.15 mm and those for the cap had a diameter of 7.45 mm. After drying, the shaped particles were stripped off and cut to the required length with sharp knives, and the caps and bodies were fitted together.

The capsules were firm and, at the same time, elastic. No dimensional changes were detectable after storage at 23° C. and 53% relative humidity for three months.

COMPARATIVE EXAMPLE

Hard capsules of size 0 were produced by the dip process. The two halves of the capsules were produced separately.

400 g of polymer of vinyl acetate and polyethylene glycol 20000 in the ratio 85:15 (Comparative Example 17) were dissolved with stirring in 600 g of demineralized water at 70° C. Care must be taken during this that no foam is produced. Into this solution were dipped vertically stainless steel pins rounded at the end and made hydrophobic with a silicone emulsion, and were withdrawn and dried in a stream of hot air at 90° C. while being continuously rotated about their own axis. The continuous rotation is important because, otherwise, the wall thickness becomes non-uniform. The pins for the body had a diameter of 7.15 mm and those for the cap had a diameter of 7.45 mm. After drying, the shaped particles were stripped off and cut to the required length with sharp knives, and the caps and bodies were fitted together.

It was possible only with difficulty to detach the caps and bodies from the stainless steel pins and fit them together. The capsules were very soft and deformable. The capsules were greatly deformed after storage at 23° C. and 53% relative humidity for three months, some of them having collapsed to a lump of polymer.

We claim:

1. A hard capsule shell comprising
(A) polymers produced by free-radical polymerization of
   a) at least one vinyl ester of $C_1$–$C_{24}$-carboxylic acids in the presence of
   b) polyether-containing compounds of formula I

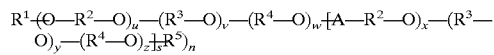

in which the variables have, independently of one another, the following meaning:
   $R^1$ hydrogen, $C_1$–$C_{24}$-alkyl, $R^6$—C(=O)—, $R^6$—NH—C(=O)—, polyalcohol residue;
   $R^5$ hydrogen, $C_1$–$C_{24}$-alkyl, $R^6$—C(=O)—, $R^6$—NH—C(=O)—;
   $R^2$ to $R^4$ —(CH$_2$)$_2$—, —(CH$_2$)$_3$—, —(CH$_2$)$_4$—, —CH$_2$—CH($R^6$)—, —CH$_2$—CHOR$^7$—CH$_2$—;
   $R^6$ $C_1$–$C_{24}$-alkyl;
   $R^7$ hydrogen, $C_1$–$C_{24}$-alkyl, $R^6$—C (=O)—, $R^6$—NH—C(=O)—;
   A —C(=O)—O, —C(=O)—B—C(=O)—O, —C(=O)—NH—B—NH—C(=O)—O;
   B —(CH$_2$)$_t$—, arylene, optionally substituted;
   n 1 to 1000;
   s 0 to 1000;
   t 1 to 12;
   u 1 to 5000;
   v 0 to 5000;
   w 0 to 5000;
   x 0 to 5000;
   y 0 to 5000;
   z 0 to 5000, and
   c) at least one other copolymerizable monomer c) selected from the group consisting of tert-butyl acrylate, methyl methacrylate, ethyl methacrylate, isobutyl acrylate, tert-butyl methacrylate, styrene, vinyl chloride, acrylic acid, methacrylic acid, acrylamide and methacrylamide, and subsequent at least partial hydrolysis of the ester functions in the original monomers a),
(B) optionally, structure-improving auxiliaries and
(C) optionally other constituents selected from the group consisting of fillers, release agents, flow aids, stabilizers, water-soluble or water-insoluble dyes, flavorings and sweeteners.

2. A hard capsule shell as claimed in claim 1, wherein the polymers (A) are obtained by free-radical polymerization of
   a) at least one vinyl ester of $C_1$–$C_{24}$-carboxylic acids in the presence of
   b) polyether-containing compounds of the general formula I with a number average molecular weight of from 300 to 100,000, in which the variables have, independently of one another, the following meaning:
   $R^1$ hydrogen, $C_1$–$C_{12}$-alkyl, $R^6$—C(=O)—, $R^6$—NH—C(=O)—, polyalcohol residue;
   $R^5$ hydrogen, $C_1$–$C_{12}$-alkyl, $R^6$—C(=O)—, $R^6$—NH—C(=O)—;
   $R^2$ to $R^4$ —(CH$_2$)$_2$—, —(CH$_2$)$_3$—, —(CH$_2$)$_4$—, —CH$_2$—CH($R^6$)—, —CH$_2$—CHOR$^7$—CH$_2$—;
   $R^6$ $C_1$–$C_{12}$-alkyl;
   $R^7$ hydrogen, $C_1$–$C_{12}$-alkyl, $R^6$—C(=O)—, $R^6$—NH—C(=O)—;
   n 1 to 8;
   s 0;
   u 2 to 2000;
   v 0 to 2000;
   w 0 to 2000; and
   c) at least one or more other copolymerizable monomers selected from the group consisting of tert-butyl acrylate, methyl methacrylate, ethyl methacrylate, isobutyl acrylate, tert-butyl methacrylate, styrene, vinyl chloride, acrylic acid, methacrylic acid, acrylamide and methacrylamide,
   and subsequent at least partial hydrolysis of the ester functions in the original monomers a).

3. A hard capsule shell as claimed in claim 1, wherein the polymers (A) are obtained by free-radical polymerization of
   a) at least one vinyl ester of $C_1$–$C_{24}$-carboxylic acids in the presence of
   b) polyether-containing compounds of the general formula I with a number average molecular weight of from 500 to 50,000, in which the variables have, independently of one another, the following meaning:
   $R^1$ hydrogen, $C_1$–$C_6$-alkyl, $R^6$—C(=O)—, $R^6$—NH—C(=O)—;
   $R^5$ hydrogen, $C_1$–$C_6$-alkyl, $R^6$—C(=O)—, $R^6$—NH—C(=O)—;
   $R^2$ to $R^4$ —(CH$_2$)$_2$—, —(CH$_2$)$_3$—, —(CH$_2$)$_4$—, —CH$_2$—CH($R^6$)—, —CH$_2$—CHOR$^7$—CH$_2$—;
   $R^6$ $C_1$–$C_6$-alkyl;
   $R^7$ hydrogen, $C_1$–$C_6$-alkyl, $R^6$—C(=O)—, $R^6$—NH—C(=O)—;
   n 1;

s 0;
u 5 to 1000;
v 0 to 1000;
w 0 to 1000; and

C) one or more other copolymerizable monomers selected from the group consisting of tert-butyl acrylate, methyl methacrylate, ethyl methacrylate, isobutyl acrylate, tert-butyl methacrylate, styrene, vinyl chloride, acrylic acid, methacrylic acid, acrylamide and methacrylamide, and subsequent at least partial hydrolysis of the ester functions in the original monomers a).

4. A herd capsule shell as claimed in claim 1, wherein the polymers (A) are obtained by free-radical polymerization of
a) at least one vinyl ester of $C_1$–$C_{24}$-carboxylic acids in the presence of
b) polyether-containing compounds of formula I

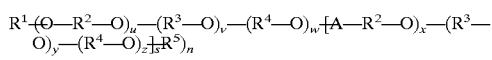

in which the variables have, independently of one another, the following meaning:

$R^1$ hydrogen, $C_1$–$C_{24}$-alkyl, $R^6$—C(=O)—, $R^6$—NH—C(=O)—, polyalcohol residue;
$R^5$ hydrogen, $C_1$–$C_{24}$-alkyl, $R^6$—C(=O)—, $R^6$—NH—C(=O)—;
$R^2$ to $R^4$ —(CH$_2$)$_2$—, —(CH$_2$)$_3$—, —(CH$_2$)$_4$—, —CH$_2$—CH($R^6$)—, —CH$_2$—CHOR$^7$—CH$_2$—;
$R^6$ $C_1$–$C_{24}$-alkyl;
$R^7$ hydrogen, $C_1$–$C_{24}$-alkyl, $R^6$—C (=O)—, $R^6$—NH—C(=O)—;
A —C(=O)—O, —C(=O)—B—C(=O)—O, —C(=O)—NH—B—NH—C(=O)—O;
B —(CH$_2$)$_t$—, arylene, optionally substituted;
n 1 to 1000;
s 0 to 1000;
t 1 to 12;
u 1 to 5000;
v 0 to 5000;
w 0 to 5000;
x 0 to 5000;
y 0 to 5000;
z 0 to 5000, and c) at least one other copolymerizable monomer selected from the group consisting of tert-butyl acrylate, methyl methacrylate, ethyl methacrylate, isobutyl acrylate, tert-butyl methacrylate, styrene, vinyl chloride, acrylic acid, methacrylic acid, acrylamide and methacrylamide, and subsequent at least partial hydrolysis of the ester functions in the original monomers a), wherein the polyether-containing compounds b) have been prepared by polymerization of ethylenically unsaturated alkylene oxide-containing monomers, alone or together with, other copolymerizable monomers.

5. A hard capsule shell as claimed in claim 1, wherein the resulting polymers are subsequently crosslinked.

6. A hard capsule shell as claimed in claim 5, wherein the resulting polymers are subsequently crosslinked by reaction with one or more compounds selected from the group consisting of dialdehydes, diketones, dicarboxylic acids, boric acid, boric acid salts, and salts of multiply charged cations.

7. A hard capsule shell as claimed in claim 1, wherein the structure-improving auxiliaries (B) employed are selected from the following classes of compounds:
a) polymers with a molecular weight greater than 50,000
b) substances which lead to crosslinking of the polymer chains of the polymers,
c) and substances which lead to crosslinking of the polymer chains of the structure-improving auxiliaries.

8. A hard capsule shell as claimed in claim 1, wherein the structure-improving auxiliaries employed are polymers selected from the group consisting of: polyamino acids, polysac-charides and synthetic polymers.

9. A hard capsule shell as claimed in claim 1, wherein the capsule consists of 10 to 100% polymers of vinyl esters on polyether, 0 to 80% structure-improving auxiliaries and 0 to 30% said other constituents.

10. A hard capsule shell according to claim 1, obtained by the dip process.

11. A hard capsule shell as claimed in claim 1 which encapsulates ingredients selected from the group consisting of one or more active pharmaceutical ingredients, vitamins, carotenoids, minerals, trace elements, food supplements, cosmetic active ingredients, crop protection agents, bath additives, perfume, flavoring, cleaner and detergent.

12. A hard capsule shell as claimed in claim 1 which capsule comprises from 20 to 80% of a polymer resistant to gastric fluid.

13. A hard capsule shell as claimed in claim 12, wherein said polymer resistant to gastric fluid is applied as a coating using pharmaceutical coating processes.

14. The hard capsule shell as claimed in claim 11 which encapsulates one or more pharmaceutical ingredients.

15. The hard capsule shell as claimed in claim 11 which encapsulates one or more ingredients selected from the group consisting of cosmetics, crop protection agents, cleaning agents and food supplements.

16. A hard capsule shell as claimed in claim 8, wherein said polyamino acids are selected from the group consisting of gelatin, zein, soybean protein and derivatives thereof.

17. A hard capsule shell as claimed in claim 8, wherein said polysaccharides are selected from the group consisting of starch, degraded starch, maltodextrins, carboxymethylstarch, cellulose, hydroxypropylmethylcellulose, hydroxypropylcellulose, hydroxypropylmethylcellulose, methylcellulose, carboxymethylcellulose, ethylcellulose, cellulose acetate, cellulose acetate phthalate, hydroxypropylmethylcellulose acetate phthalate, hydroxypropylmethylcellulose acetate succinate, hemicellulose, galactomannans, pectins, alginates, carrageenans, xanthan, gellan, dextran, curdlan, pullulan, gum arabic, chitin, and derivatives thereof.

18. A hard capsule shell as claimed in claim 8, where said synthetic polymers are selected from the group consisting of polyacrylic acid, polymethacrylic acid, copolymers of acrylic esters and methacrylic esters, polyvinyl alcohols, polyvinyl acetate, polyethylene glycols, polyoxyethylene/polyoxypropylene block copolymers, polyvinylpyrrolidones and derivatives thereof.

* * * * *